United States Patent [19]
Kaye et al.

[11] 3,939,823
[45] Feb. 24, 1976

[54] ESOPHAGEAL TRANSDUCER

[75] Inventors: Michael D. Kaye, Burlington, Vt.; Kingsley Carlton Rock, Jr., Littleton, Colo.; Charles E. Johnson, Denver, Colo.; J. Philip Showalter, Denver, Colo.

[73] Assignee: The United States of America as represented by the Department of Health, Education and Welfare, Washington, D.C.

[22] Filed: Jan. 28, 1975

[21] Appl. No.: 544,932

[52] U.S. Cl.......... 128/2 S; 73/398 AR; 128/2.05 D; 128/2.05 E
[51] Int. Cl.²............................................ A61B 5/10
[58] Field of Search ............ 128/2 S, 2 R, 2 M, 2 P, 128/2.05 E, 2.05 D; 73/398 AR, 406

[56] References Cited
UNITED STATES PATENTS

| | | | |
|---|---|---|---|
| 3,437,088 | 4/1969 | Bielinski | 128/2 S |
| 3,480,003 | 11/1969 | Crites | 128/2 S |
| 3,710,781 | 1/1973 | Hutchins et al. | 128/2.05 D |
| 3,811,427 | 5/1974 | Kresse | 128/2.05 D |
| 3,811,429 | 5/1974 | Fletcher | 128/2.05 E |
| 3,831,588 | 8/1974 | Rindner | 128/2.05 E |

FOREIGN PATENTS OR APPLICATIONS

| 790,091 | 9/1935 | France | 128/2 S |
|---|---|---|---|

*Primary Examiner*—Kyle L. Howell
*Attorney, Agent, or Firm*—Browdy and Neimark

[57] ABSTRACT

An esophageal transducer measures pressure due to esophageal contractions. The transducer is inserted into the esophagus at the end of a catheter. The transducer is fully contained within a housing at the end of the catheter and is capable of measuring pressure variations at all points about its entire circumference. The housing has a flexible portion extending around its entire circumference which encloses a fluid-filled section. The fluid of the fluid-filled section contacts a pressure-sensitive piezoelectric material which produces an electrical output indicative of pressure changes in the fluid-filled section.

9 Claims, 5 Drawing Figures

ESOPHAGEAL TRANSDUCER

FIELD OF THE INVENTION

The invention relates to the measurement of pressure, and, more particularly, to a transducer for measuring pressure due to esophageal contractions, which is fully contained within a transducer housing inserted into the esophagus at the end of a catheter.

BACKGROUND OF THE INVENTION

In the field of the diagnosis of various ailments of the esophageal region of the body, such as achalasia, scleroderma, spasm, hiatal hernia, etc., the measurement of the pressure in the esophagus can be very helpful.

Insertion of a catheter having a piezoelectric transducer mounted thereon to measure pressures in internal body cavities such as the esophagus is known in the presently existing art. One such of a flexible tube has at least one piezoelectric transducer mounted on the outer surface of the flexible tube. The transducer arrangement on the catheter is for a transducer which is only sensitive to an area on the surface of the flexible tube which corresponds to less than one-half the circumference of the flexible tube. Furthermore, the configuration of the apparatus is of a transducer diaphragm, which is mounted on the external portion of the flexible tube and, therefore, is susceptible to certain inaccuracies created when only a portion of the transducer diaphragm is in contact with the surface of the internal body cavity into which the flexible tube catheter is inserted.

It would, therefore, be desirable to have a transducer which is insertable on a catheter, which transducer is sensitive to pressure variations about the entire circumference of the catheter. In addition, it would be desirable to have a housing for the transducer such that the diaphragm of the transducer does not itself contact the walls of the internal body cavity into which the catheter is inserted.

SUMMARY OF THE INVENTION

It is, therefore, an object of the present invention to alleviate the shortcomings of the pressure measuring devices of the prior art.

It is a further object of the present invention to provide for better pressure measurement within internal body cavities.

It is an additional object of the present invention to provide a transducer for internal body cavity pressure measurement which is mounted on a catheter and which transducer is sensitive to pressure variations about the entire circumference thereof.

It is still a further object of the present invention to provide a catheter transducer device for internal body cavity pressure measurement which prevents the diaphragm of the transducer from contacting the wall of the internal body cavity into which the catheter is inserted.

The above and other objects of the present invention are accomplished by constructing a transducer device which may consist of a two-part housing, one part of which may be bullet-shaped to facilitate insertion into the internal body cavity. The two parts of the housing may be joined together by suitable means such as a plurality of steel pins such that there is a separation between the two parts of the housing at the junction thereof. The housing is connected to a catheter which contains therein electrical connections. The part of the two-part housing which is connected to the catheter also contains a transducer, e.g., a semiconductor strain gage, with a cavity which has an opening into the area of the steel pins. The area containing the steel pins is closed by a flexible sleeve and contains a fluid medium for transferring pressure from the entire circumference of the transducer housing to the transducer contained within the cavity.

For a better understanding of the invention, a possible embodiment thereof will now be described with reference to the attached drawing, it being understood that this embodiment is merely exemplary and not limitative.

BRIEF DESCRIPTION OF THE DRAWING

The above and other objects and the nature and advantages of the present invention will be more fully understood by the detailed description of illustrated embodiments with reference to the drawing wherein.

DETAILED DESCRIPTION OF PREFERRED EMBODIMENTS

Figure 1:
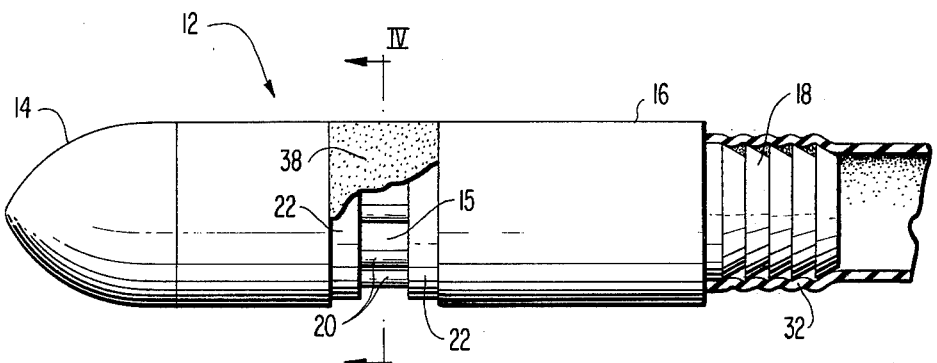
FIG. 1 is a side elevational view of an embodiment of an assembled transducer housing of the present invention.

Referring to FIG. 1, a transducer assembly housing 12 of the present invention is seen to be comprised of a first portion 14 and a second portion 16. The second portion 16 has a fitting 18, e.g., screw threads or a friction fitting, for connecting the transducer housing assembly 12 to a catheter 32. The first portion 14 is located most distally on the transducer housing assembly 12 from the catheter, and may be bullet-shaped as shown in FIG. 1 in order to facilitate insertion into an internal body cavity.

The first portion 14 and second portion 16 of the transducer housing assembly 12 of the present invention are joined together by steel pins 20 in order to form a cavity 15 between the first portion 14 and the second portion 16. The first portion 14 and second portion 16 each have a recessed section 22. A sleeve 38 made of suitable flexible material, such as silicone rubber (e.g., Silastic) is cemented to the recessed areas 22 in order to cover the cavity 15 created by steel pins 20 separating the first portion 14 and second portion 16. The second portion 16 has a semiconductor transducer 30 mounted therein noting FIG. 5, as more fully described below, which is in pressure communication with the cavity 15 between the portions 14 and 16, which cavity 15 may be filled with a pressure transmitting fluid, such as silicone oil, which permits pressure variations created in the cavity by the flexing of the flexible sleeve 38 to the transducer 30 contained within the second portion 16.

Figure 2:
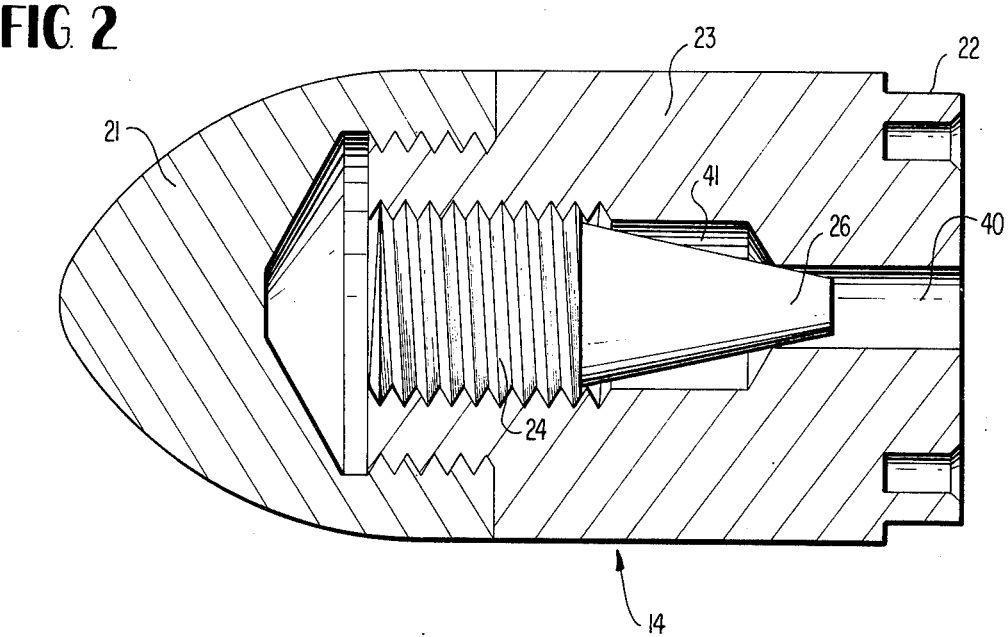
FIG. 2 is a side elevational cut-away view of one portion of the transducer housing of the embodiment of FIG. 1.

Referring to FIG. 2, the first portion 14 of the transducer housing assembly 12 of the present invention is shown to be made up of a body member 23 and a nose member 21. The body member 23 has an internal screw-threaded passage 41 which joins with an internal tubular passage 40, which in turn communicates with the cavity 15. A tapered sealing member 26, having screw threads 24, is threaded into the passage 41 such that the stop member 26 seals the passage 40 in order to prevent pressure variations within the cavity 15 due to internal leakage of the pressure transfer fluid; the tapered body of the sealing member 26 with its seat in the bore of the body member 23 enables the oil chamber to be sealed without pressure to the sensing element. The bullet-shaped nose 21 may then be threaded onto the body member 23 in order to facilitate the insertion of the transducer housing assembly 12 into the internal body cavity.

Figure 3:
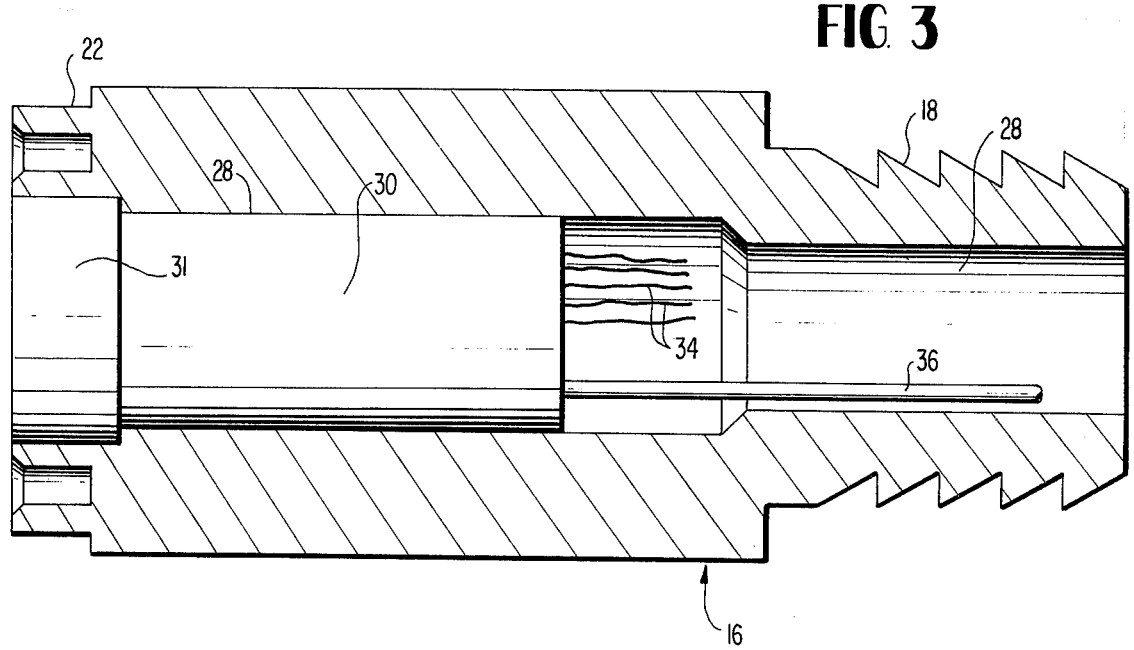
FIG. 3 is a side elevational cut-away view of a second portion of the transducer housing of the embodiment of FIG. 1.

Referring to FIG. 3, the second portion 16 of the transducer housing assembly 12 of the present invention is shown to contain a hollow passage 28 into which is inserted the transducer 30 having a diaphragm section 31, the face of the diaphragm 31 being perpendicular to the axis of the housing; the transducer 30 may be a semiconductor strain gage such as model CQML-125-10 manufactured by KULITE. The main body of the transducer sensing element 30 is fixed into the channel 28 such as with epoxy resin and is sealed with a suitable sealant such as silicone rubber, e.g., RTV Silastic, around the circumference of the diaphragm section 31 of the sensing element 30.

Electrical connectors 34 pass through the hollow channel 28 in the connecting ferrule end 18 of the second portion 16. These electrical connectors are passed through the catheter 32 to a pressure measuring device, including an amplifier and readout device, outside of the body. Also, since the pressure measurements are desirably referenced to atmospheric pressure, a hollow tube 36 provides an air path to supply atmospheric reference pressure to the pressure sensing element 30.

Figure 4:
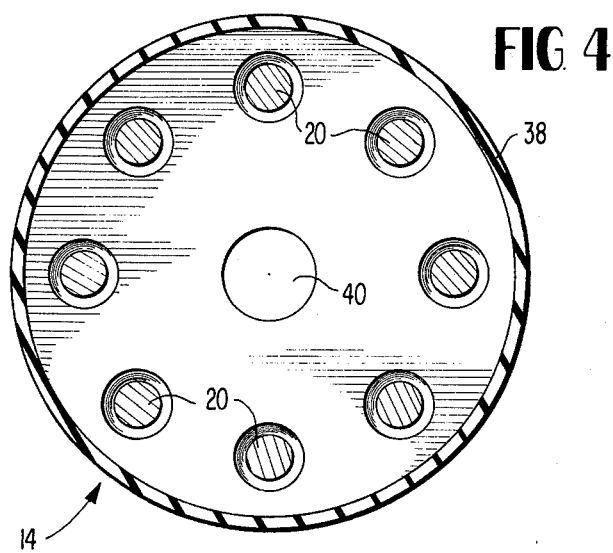
FIG. 4 is a cross-sectional view of the transducer housing taken along lines IV—IV of FIG. 1.

Referring to FIG. 4, the arrangement of the steel pins 20 in the body of first portion 14 can be seen. As shown, the steel pins 20 serve to connect the first portion 14 and the second portion 16 such that the steel pins join the first portion 14 and second portion 16 without interferring with the flexing of the flexible sleeve 38.

The apparatus of the present invention is constructed by fabricating the first and second portions 14, 16 and the sensing element 30. The sensing element 30 is then affixed into the hollow opening 28 of second portion 16. The stainless steel pins 20 are then inserted into the first portion 14 and the second portion 16 and the second portion 16 is then pressed onto the stainless steel pins 20.

The Silastic sleeve 38 is then cemented around the recessed area 22 of the first and second portions 14, 16 and a silicone oil is then placed into the cavity thus formed, such that it fills the space closed by the Silastic sleeve and contacts the sensing element 30. The transducer unit is then placed in a vacuum oven and the temperature raised to approximately 100°C, while the oven is evacuated to remove the air bubbles from the silicone oil.

The element 12 is then removed from the vacuum oven and the sealing member 26 is carefully screwed into hollow threaded opening 41 of the first element 14, while monitoring the sensing element 30 to be certain that high pressures are not applied to the sensing element 30, until the sealing member 26 is fully seated as shown in FIG. 2. Final assembly includes screwing the bullet-shaped end 21 onto the body member 23 and attaching the catheter tube 32 to the connector 18 of the ferrule end of the transducer housing assembly 12.

Figure 5:
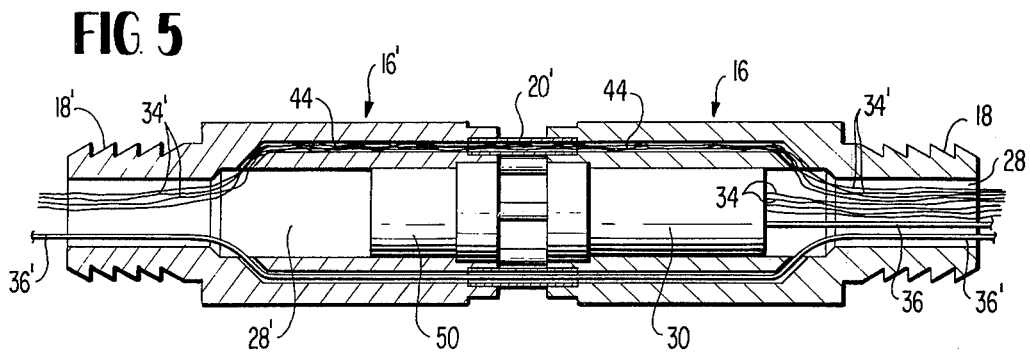
FIG. 5 is a cross-sectional view of a second embodiment.

A second embodiment of the present invention is shown in FIG. 5 which may be used when it is desired to attach more than one pressure sensing element 30 to a single catheter. This may be accomplished as shown in FIG. 5 by replacing first portion 14 of the FIG. 2 device with a duplicate portion 16' constructed substantially identically to second portion 16. In this embodiment, one or more of the steel pins 20' may be hollow. Channels 44 extend through the body of the second portion 16 and the first portion 16' from the hollow steel pins 20' to the hollow channels 28', 28 respectively of the portion 16' and the portion 16. The hollow channels 44 may provide a passageway for electrical connectors 34' and also for air pressure through pressure equalizing tube 36'.

When this construction is used a further short length of catheter is attached to the connector 18' of the ferrule end of first portion 16' and an identical unit to that shown in FIG. 5 may be then attached to the other half of this short length of catheter. A plug member 50 preferably similar to the sealing member 26 with tapered plug and seat, may be used to seal the hollow opening 28' of the first element 16' in order to insure functioning of the pressure transfer fluid medium contained with the Silastic sleeve, not shown, between portion 16' and portion 16.

From the above description it can thus be seen that the present invention provides a pressure transducer for insertion into internal body cavities which is capable of measuring pressure about the entire circumference of the pressure transducer housing assembly 12. Means are provided for equalizing the pressure of each individual pressure sensing element with atmospheric pressure outside of the body and electrical connections are provided between each transducer and a pressure measuring device outside of the body. In addition the pressure transducer housing assembly is small and compact, easily attached to a catheter, and easily inserted within a body cavity. Also, the present invention has the capability of attaching more than one pressure transducer housing assembly to a single catheter.

The embodiments described above are particularly designed for use in the gastrointestinal environment which is extremely acid. Accordingly, the transducer body is preferably made of stainless steel and the sleeve and sealant are of silicone material, so that the device will be fully resistant to the hostile environment. It will be understood, however, that a device in accordance with the present invention for use in less hostile environments may be formed of less resistant materials.

It will be obvious to those skilled in the art that various changes may be made without departing from the scope of the invention and the invention is not to be considered limited to what is shown in the drawings and described in the specification.

What is claimed is:

1. A pressure sensing device for measuring pressure circumferentially in internal body cavities comprising:
    a catheter for introducing said pressure sensing device into the internal body cavities,
    a rigid cylindrical transducer housing connected to said catheter and defining an open cavity therein spaced along the length thereof, said housing having a distal end, pressure sensing means, mounted entirely within said housing and in pressure communication with said cavity, for generating an electrical signal in response to pressure in said cavity, means for sensing the pressure impinging on said transducer housing circumferentially comprising an annular flexible sleeve member contacting said housing coaxial therewith and surrounding said cavity, a liquid medium contained within said cavity and in contact with said flexible sleeve and said pressure sensing means for transferring pressure from the entire circumference of said flexible sleeve member to said pressure sensing means, electrical transmitting means connected to said pressure sensing means and passing through the distal end of said housing and passing through said catheter for transmitting said electrical signal to a receiver external to the body.

2. The pressure sensing device as recited in claim 1 wherein said housing further includes:
a first portion and a second portion;
joining means for joining said first portion and said second portion such that said first and second portions do not contact each other;
said flexible sleeve extending between said first and second portions, thereby forming said cavity; and
said pressure sensing means comprising a pressure transducer contained in said first portion, and having a pressure sensitive element in contact with said liquid medium in said cavity.

3. The pressure sensing device as recited in claim 2 wherein said pressure sensing means is a semiconductor strain gage having a diaphragm and said diaphragm comprises said pressure sensitive element.

4. The pressure sensing device as recited in claim 2 wherein said flexible sleeve is composed of silicone rubber.

5. The pressure sensing device as recited in claim 2 wherein said liquid medium is silicone oil.

6. The pressure sensing device as recited in claim 2 further comprising a second transducer housing attached to said first transducer housing, said housings having a common longitudinal axis.

7. The pressure sensing device as recited in claim 6 further including pressure equalizing means connected to one of said transducer housings and passing through said catheter for supplying an atmospheric reference pressure to said transducer housing, and wherein said joining means contains at least one hollow tube providing a passageway for said electrical transmitting means for transmitting electrical signals and said pressure equalizing means.

8. The pressure sensing device as recited in claim 1 further comprising a second transducer housing attached to said first transducer housing, said transducer housings having a common longitudinal axis.

9. The pressure sensing device as recited in claim 1 further including pressure equalizing means connected to said pressure sensing means and passing through said catheter for supplying an atmospheric reference pressure to said pressure sensing means.

* * * * *